(12) United States Patent
Work et al.

(10) Patent No.: US 6,749,580 B2
(45) Date of Patent: Jun. 15, 2004

(54) CATHETER

(75) Inventors: Jack Work, Atlanta, GA (US); Claudio Ronco, Vicenza (IT); Angela Gloukhoff, Harleysville, PA (US)

(73) Assignee: Medical Components, Inc., Harleysville, PA (US)

( * ) Notice: Subject to any disclaimer, the term of this patent is extended or adjusted under 35 U.S.C. 154(b) by 255 days.

(21) Appl. No.: 10/057,340

(22) Filed: Jan. 23, 2002

(65) Prior Publication Data

US 2003/0069534 A1 Apr. 10, 2003

Related U.S. Application Data

(60) Provisional application No. 60/327,515, filed on Oct. 5, 2001.

(51) Int. Cl.⁷ ............................ A61M 1/00; A61M 25/00
(52) U.S. Cl. ........................................ 604/29; 604/284
(58) Field of Search ........................ 604/27–30, 35, 604/39, 43, 272, 274, 94.01, 523, 284

(56) References Cited

U.S. PATENT DOCUMENTS

| | | |
|---|---|---|
| 3,707,967 A | 1/1973 | Kitvilakis et al. |
| 4,437,856 A | 3/1984 | Valli |
| 4,671,795 A | 6/1987 | Mulchin |
| 4,681,564 A | 7/1987 | Landreneau |
| 4,925,452 A * | 5/1990 | Melinyshyn et al. ....... 604/284 |
| 4,935,004 A | 6/1990 | Cruz |
| 4,941,872 A | 7/1990 | Felix et al. |
| 5,057,075 A | 10/1991 | Moncrief et al. |
| 5,143,062 A | 9/1992 | Peckham |
| 5,254,084 A | 10/1993 | Geary |
| 5,322,521 A * | 6/1994 | Wilk ........................... 604/317 |
| 5,458,582 A * | 10/1995 | Nakao ......................... 604/264 |
| 5,599,304 A * | 2/1997 | Shaari ........................ 604/94 |
| 5,607,462 A | 3/1997 | Imran |
| 5,776,111 A | 7/1998 | Tesio |
| 6,001,078 A | 12/1999 | Reekers |
| 6,001,079 A | 12/1999 | Pourchez |
| 6,241,710 B1 | 6/2001 | VanTassel et al. |
| 6,245,039 B1 | 6/2001 | Brugger et al. |
| 6,409,699 B1 | 6/2002 | Ash |

OTHER PUBLICATIONS

R. Amerling, C. Ronco and N.W. Levin; Continuous Flow Peritoneal Dialysis; Peritoneal Dialysis International; May 2000; p. S172–177; vol. 20, Supplement 2; Multimed, Inc., Milton, Ontario, Canada.

(List continued on next page.)

*Primary Examiner*—Sharon Kennedy
(74) *Attorney, Agent, or Firm*—Joseph E. Maenner; Monte & McGraw, P.C.

(57) ABSTRACT

Continuous flow catheters, diffusers for catheters, catheters having a diffuser, and methods for continuous flow peritoneal dialysis are provided. The continuous flow catheter includes at least two lumens, of which one is short and the other is long. The long lumen is coiled and contains a plurality of openings. Another similar continuous flow catheter also includes a diffuser for the dispensing of fluid in a diffused manner. The catheters are used for peritoneal dialysis. The diffuser, for use with a catheter, has a plurality of openings for the dispensing of matter in a diffused manner. One method for continuous flow peritoneal dialysis includes creating an incision in the body of the user and separating the anatomical layers, making a circular suture in the peritoneal membrane, making an incision in the peritoneal membrane, inserting the catheter, and tightening the parietal peritoneum. Another method additionally includes anesthetizing the skin and peritoneal surface, making a lateral incision in the skin of the user, creating a skin tunnel, passing the catheter through the skin tunnel, connecting attachments to the catheter, and suturing the skin incision. The methods also include providing a catheter having a diffuser.

41 Claims, 8 Drawing Sheets

OTHER PUBLICATIONS

C. Ronco and J.A. Diaz–Buxo; Automated Peritoneal Dialysis; Nephron; Jan. 18, 2001; p. 1–7; vol. 87, No. 1; S. Karger AG, Basel, Switzerland.

C. Ronco, A. Gloukhoff, R. Dell'Aquila and N.W. Levin; Catheter Design for Continuous Flow Peritoneal Dialysis; Blood Purification; Jan. 17, 2002; pp. 40–44; vol. 20, No. 1; S. Karger AG, Basel, Switzerland.

International Preliminary Examining Authority Written Opinion mailed Aug. 29, 2003.

International Search Report mailed May 8, 2003.

\* cited by examiner

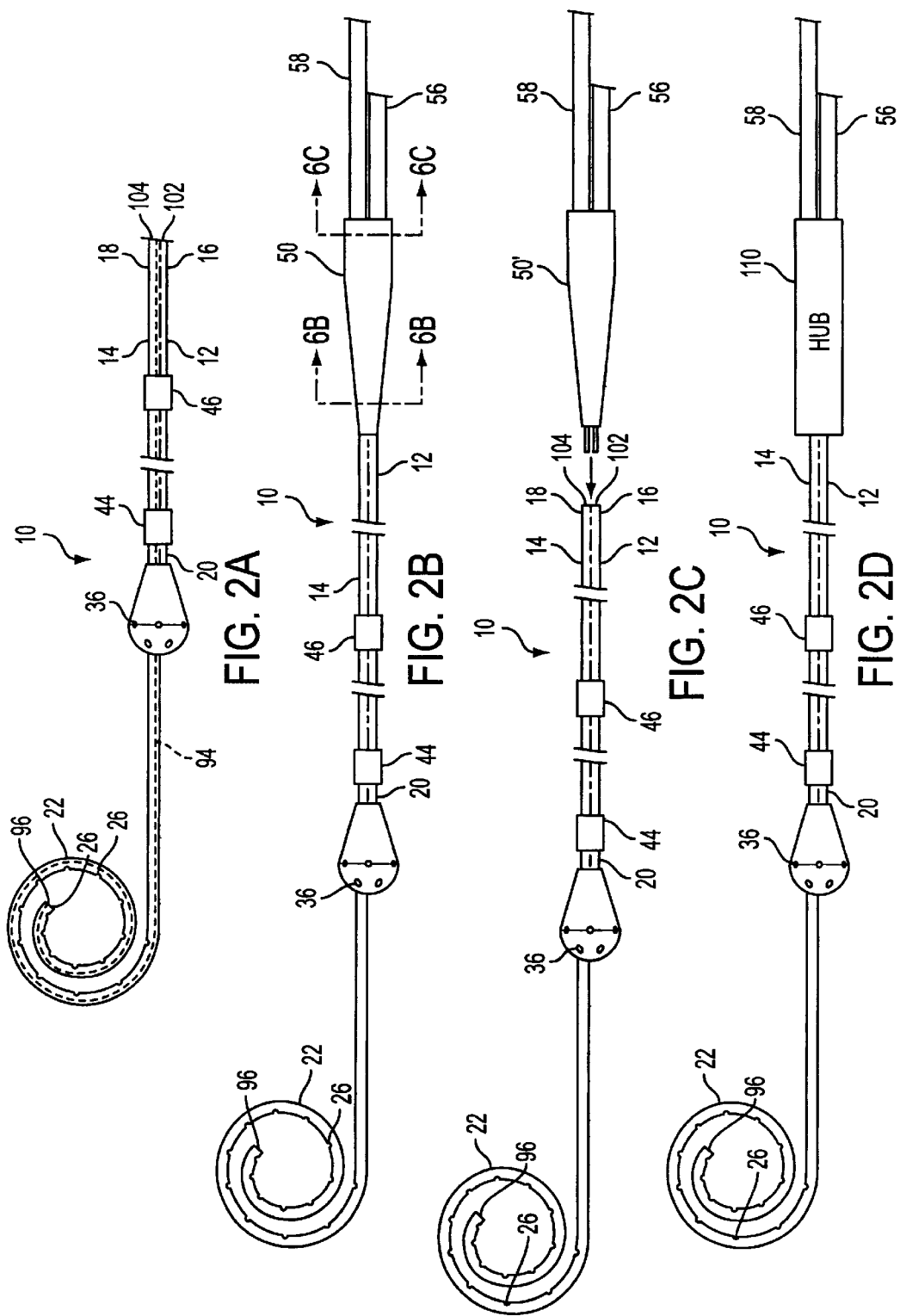

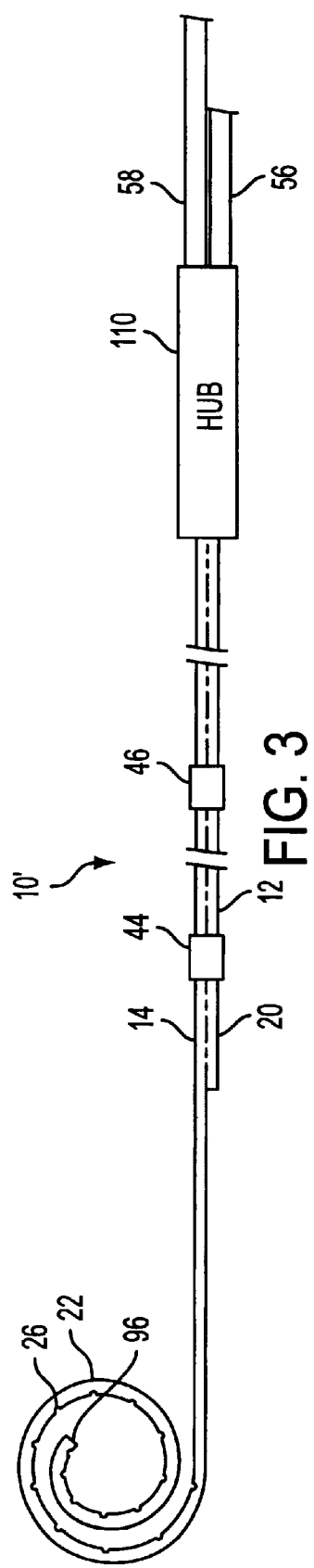
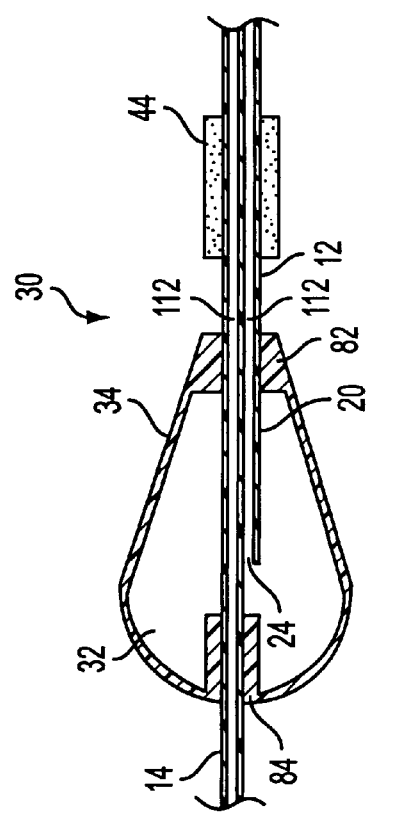

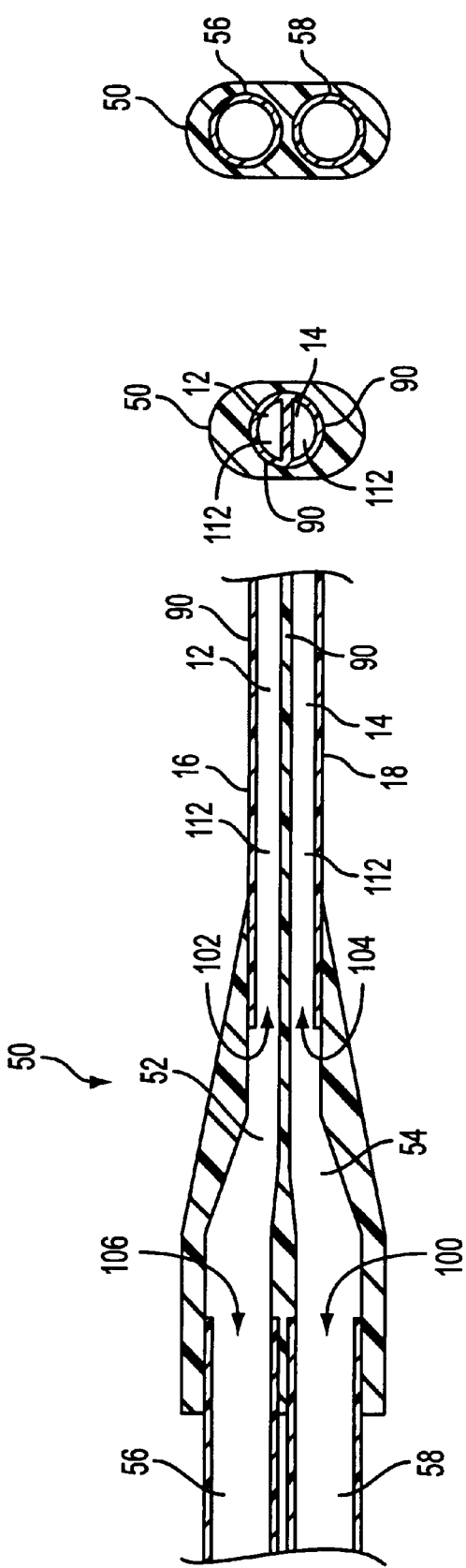

CATHETER

CROSS-REFERENCE TO RELATED APPLICATION

This application claims the benefit of U.S. Provisional Application Ser. No. 60/327,515, filed on Oct. 5, 2001, entitled "Continuous Flow Peritoneal Dialysis," of which Claudio Ronco and Angela Gloukhoff are the inventors.

BACKGROUND OF THE INVENTION

Continuous flow peritoneal dialysis is a technique which utilizes a certain amount of fluid, generally dialysate, which is constantly present in the abdomen. Continuous flow peritoneal dialysis previously known in the art has utilized two single lumen peritoneal dialysis catheters or a modified large bore hemodialysis catheter. The inflow and uptake catheters enable the inflow and outflow to remain constant. However, high dialysate flow rates and re-circulation due to channeling or poor mixing inside the peritoneal cavity are problems associated with continuous flow peritoneal dialysis.

In the continuous flow peritoneal dialysis technique, the peritoneal dialysis solution is either utilized in a single pass or a re-circulation loop. Various re-circulation systems, such as sorbent cartridges or dialyzers, are known. A problem has been the quick drainage of fresh solution before coming into contact with the peritoneal exchange surface.

Regeneration systems include utilizing a batch of moderate volume prepared fluid and re-circulating the fluid until it saturates. Another method provides an initial fixed volume of commercial dialysis solution for priming, followed by continuous regeneration of the spent dialysate. Regeneration can be performed either by a hemodialysis filter or by absorption. Another method is preparation of solutions from water in concentrate with on-line ultra-filtration.

The proximal ends of the two lumens are attached to a dialysate regeneration means. Regenerated dialysate, or fresh dialysate, are introduced into the abdomen through one of the catheters, which is connected to a means for providing regenerated or fresh dialysate, which is well known in the art.

For all of the aforementioned reasons, it is important to have a continuous flow peritoneal dialysis catheter and method which effectively allow the dialysate to mix into the peritoneum while reducing trauma to the peritoneal walls. In addition, it is important to have catheters, and diffusers for catheters, that gently dispense the matter flowing through the catheter.

SUMMARY OF THE INVENTION

The present invention relates generally to continuous flow catheters with at least two lumens, one of which is a short lumen, and the other of which is a long lumen. In this invention, the long lumen, which is the uptake lumen, is coiled. It may have a plurality of openings, generally located on the inside of the coil, for the intake of matter flowing through the catheter.

The catheter also may include a diffuser, which is located over the distal end of the short lumen, for dispensing matter into the body of the user. The long lumen may extend beyond, and/or through, the diffuser.

The catheter may also include a hub at the proximal ends of the at least two lumens. The hub may be passable subcutaneously through the body of the user of the catheter, or the hub may be detachable.

The catheter of the current invention may be used for peritoneal dialysis.

In addition, the catheter may include at least one cuff located proximally to the peritoneal membrane for the adherence of subcutaneous tissue. The catheter may contain lumens which are "D" shaped.

The current invention also relates to diffusers for a catheter, as well as catheters having a diffuser. The diffuser has an interior portion and an exterior portion and at least one opening for the dispensing of matter into the body of the user. In addition, the diffuser may have a plurality of openings through which the matter may be dispensed into the body of the user in a diffused manner. The plurality of openings may be located radially around the sides of the diffuser in a generally perpendicular manner to the longitudinal axis of the catheter. The shapes of the diffuser generally consist of cylindrical, teardrop, bell, round, oval, semi-round, semi-oval and a combination of shapes. The diffuser, and catheter having a diffuser, may be used on a catheter used for a continuous flow peritoneal dialysis.

The current invention also includes methods for continuous flow peritoneal dialysis which include the steps of creating an incision in the body of the user and separating the anatomical layers, making a circular suture in the peritoneal membrane, making an incision in the peritoneal membrane, inserting the catheter, and tightening the parietal peritoneum. The method also may include anesthetizing the skin and peritoneal surface. In addition, the method may include making a lateral incision in the skin of the user, creating a skin tunnel, passing the catheter through the skin tunnel, connecting attachments to the catheter, and suturing the skin incision. The method may also include providing a catheter having a diffuser.

BRIEF DESCRIPTION OF THE DRAWINGS

The accompanying drawings, which are incorporated in and form a part of the specification, illustrate the embodiments of the present invention, and together with the description, serve to explain the principles of the invention. In the drawings, the same reference numerals are employed for designating the same elements throughout the several figures.

FIG. 1C-2 is a perspective view of a semi-round shaped diffuser having a round shaped long lumen;

FIG. 2A is a top elevational view of a catheter with a diffuser and with no hub;

FIG. 2B is a top elevational view of a catheter with a diffuser and a hub;

FIG. 2C is a top elevational view of a catheter with a diffuser and a detachable hub;

FIG. 2D is a top elevational view of a catheter with a diffuser and with an optional hub of any kind;

FIG. 3 is a top elevational view of a catheter without a diffuser and with an optional hub of any kind;

FIG. 4 is a cross section of a diffuser;

FIG. 6A is a cross section of a hub;

FIG. 6B is a cross section of the double "D" lumens in the hub;

FIG. 6C is a cross section of the extenders in the hub;

DETAILED DESCRIPTION OF THE INVENTION

Figure 1A:
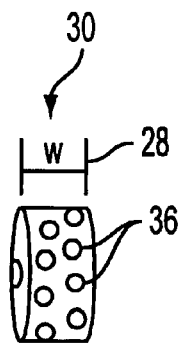
FIG. 1A is a perspective view of a cylindrically shaped diffuser.

In describing embodiments of the invention illustrated in the drawings, specific terminology will be used for the sake of clarity. However, the invention is not intended to be limited to the specific terms so selected, and it is to be understood that each specific term includes all technical equivalents which operate in a similar manner to accomplish a similar purpose. The words "proximal," "distal," "short" and "long" are used herein for exemplary purposes, and are not to be taken as a limitation on the present invention. The words "proximal" and "distal" refer to directions away from and closer to, respectively, the insertion tips of the first and second lumens according to the present invention. The words "short" and "long" designate the length of lumens relative to one another.

Reference is now made to FIGS. 2A, 2B, 2C, 2D, and 3 which show the catheter 10, 10' of the current invention. As seen in these figures, the catheter contains at least two lumens, a first lumen 12 and a second lumen 14. The second lumen 14 is longer than the first lumen 12. For explanatory purposes, the second lumen 14 also is referred to as a long lumen 14 and the first lumen 12 also is referred to as a short lumen 12. Each lumen has a proximal end 16, 18 and a distal end region, 20, 22. Each of the distal end regions, 20, 22 of each of the at least two lumens 12, 14 has at least one opening 24, 26 for the passage of matter 42 into or out of the body of the user of the catheter 10, 10'. Matter 42 passes through the longitudinal lumen channel 112 defined by the lumen wall 90.

The catheter 10, 10' of the present invention can be adapted for use in various applications in which bodily fluids, medicaments or other solutions are introduced into and removed from the body such as perfusion, infusion, plasmapheresis, hemodialysis, chemotherapy, and the like. The area to be catherized may be the peritoneum, and may be any suitable area within the body. Other areas in which the catheter 10, 10' may be used include, for example, any abscess cavity, post-operative cavity, and other areas of the body including inter-abdominal, sub-diaphragmatic and sub-hepatic areas. It should be understood by one of ordinary skill in the art from this disclosure that these areas are exemplary, and that the catheter 10, 10' may be used to remove or introduce matter in various areas to be catherized. In addition, it will be understood by one skilled in the art based on this disclosure, that the catheter 10, 10' can be configured and adapted by increasing or decreasing the catheter size and/or number of catheters and/or lumens such that the catheter 10, 10' can be beneficially used for other medical applications in which matter is introduced into and/or removed from the body.

Matter 42 may pass into the body of the user of the catheter through the short lumen 12, which also can be referred to as the delivery lumen. Matter may be removed from the body of the user of the catheter 10 through the long lumen 14, which also can be referred to as the uptake or return lumen. However, it is to be understood that within the scope of the invention the long lumen 14 also may be a delivery lumen and the short lumen 12 may be an uptake lumen.

The long lumen 14 can be coiled and has at least one opening 26 for the passage of matter through the lumen. The at least one opening 26 can be at the distal end 96 of the lumen 14. In addition, it is within the scope of this invention to place the at least one distal opening 26 along the side 98 of the distal end region 22 of the long lumen 14.

The long lumen 14 may have a plurality of openings 26 along the side 98 of the distal end region 22 of the lumen.

Figure 8A:
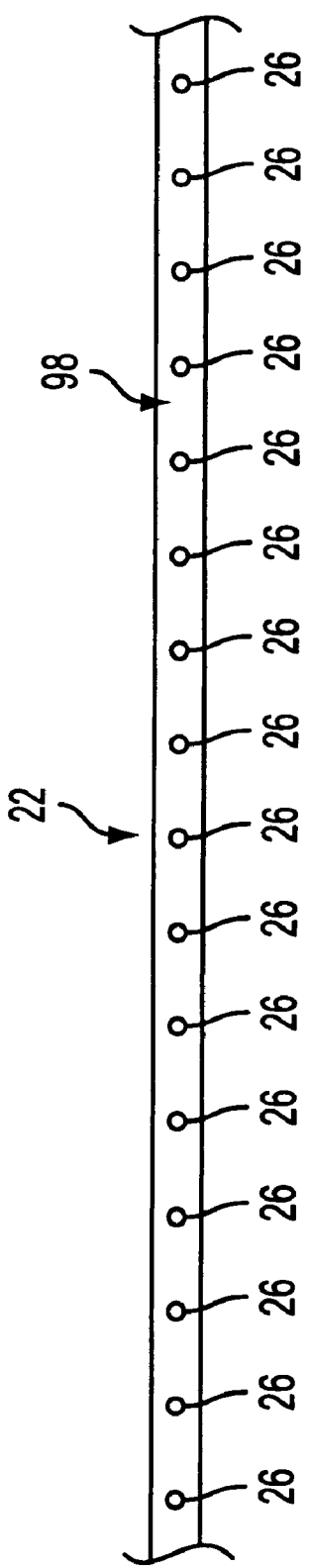
FIG. 8A is a side view of the long lumen extended.

The plurality of openings 26 also may be located along the side 98 of the distal end region 22 of the lumen in a manner whereby all of the plurality of openings 26 are located on the inside of the coiled distal end region 22 of the lumen. FIG. 8A, which extends the coil for exemplary purposes, illustrates this embodiment. In addition, a distal opening 26, optionally may be included at the end 96 of the distal end region 22 of the lumen 14.

Figure 8B:
FIG. 8B is a cross section showing two double "D" shaped lumens.
Figure 8C:
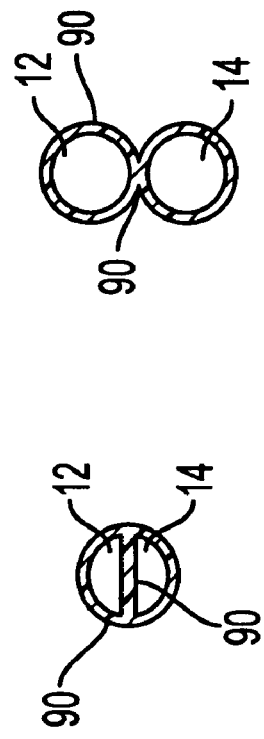
FIG. 8C is a cross section showing two round shaped lumens.

As seen in FIG. 8B, the lumens 12, 14 each may have a "D" shape. However, it is within the scope of the invention to have lumens 12, 14 that are round in shape, as seen in FIG. 8C. The lumen 12, 14 shapes as shown in FIGS. 8B and 8C are intended to be exemplary only of the variety of lumen shapes that can be used with the present invention. It will be understood, based on this disclosure, that the present invention is not limited to the configurations shown in FIGS. 8B and 8C. One skilled in the art will appreciate that all shapes of the lumens known in the art and to be discovered are within the scope of the invention. In addition, the lumens each may have shapes and sizes that vary from the other lumen or lumens.

Optionally, as known in the art, a radiopaque strip 94 may be included in the lumen wall 90 of either the short lumen 12 or the long lumen 14 to distinguish the lumens from one another, particularly at their proximal ends 16, 18. Generally, the radiopaque strip 94 will be placed in the long lumen 14 as the longer length enables the user to more readily identify the radiopaque strip 94.

Figure 1B:
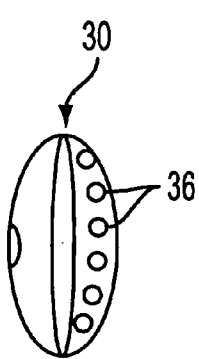
FIG. 1B is a side elevational view of a round and/or oval diffuser.
Figures 1, 1C:
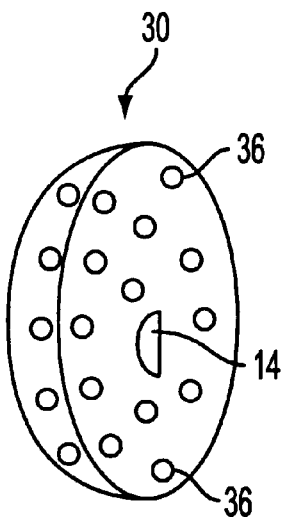
FIG. 1C-1 is a perspective view of a semi-oval shaped diffuser having a "D" shaped long lumen.

Reference is now made to FIGS. 1A through 1E, 2A through 2D, 4, 5A and 5B, which illustrate a diffuser 30. It is to be noted that the embodiment of the catheter 10' that is illustrated in FIG. 3 does not contain a diffuser. The diffuser 30 may be added to the catheter 10 and located over the at least one distal opening 24 in the short lumen 12. The long lumen 14 extends beyond the diffuser 30 more distally into the body of the user of the catheter. As seen most clearly in FIGS. 1C-1, 1C-2, and 4, the long lumen 14 may extend through the diffuser 30. In FIGS. 1C-1, the long lumen 14 is "D" shaped. In FIGS. 1C-2, the long lumen 14 has a round shape.

The diffuser 30 has an interior portion 32 and an exterior portion 34 and at least one opening 36 between the interior portion 32 and the exterior portion 34. The matter 42 being dispensed in the body of the user flows through the short lumen 12 and into the diffuser 30 at the distal end opening 24 of the lumen 12. Thereafter, the matter 42 flows through the at least one opening 36 of the diffuser and into the body of the user.

The diffuser 30 may have a plurality of openings 36 through which the matter 42 enters the body of the user in a diffused manner. In addition, the plurality of openings 36 may be located radially around the sides of the diffuser 30 in a generally perpendicular manner to the longitudinal axis of the catheter 10.

The catheter 10 of the current invention may be used for continuous flow peritoneal dialysis. In peritoneal dialysis, the matter 42 flowing through the catheter may be dialysate. The diffuser 30 of the current invention enables a gentle interaction on the peritoneal structures from the effects of high dialysate flow rates, and enables the dialysate solution to readily mix into the peritoneal cavity 40. When used for continuous flow peritoneal dialysis, the radially located openings 36 allow dialysate 42 to exit perpendicularly generally 360 degrees from the diffuser.

Figures 1, 1C, 2:
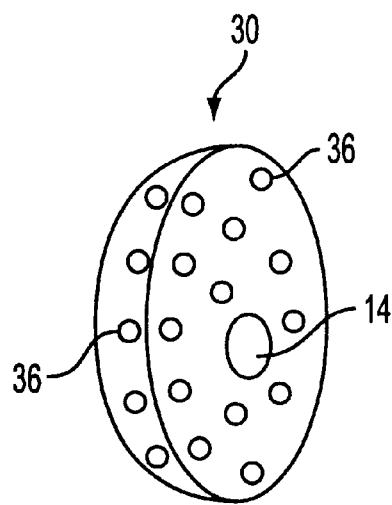
Figure 1D:
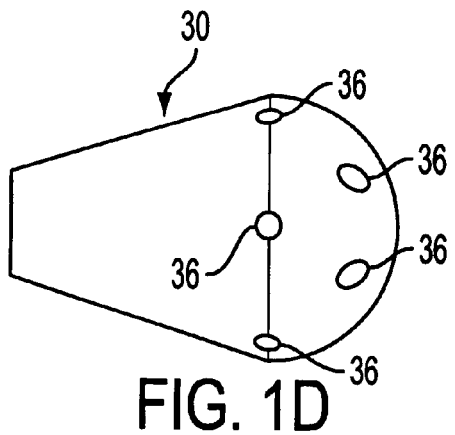
FIG. 1D is a perspective view of a teardrop shaped diffuser.
Figure 1E:
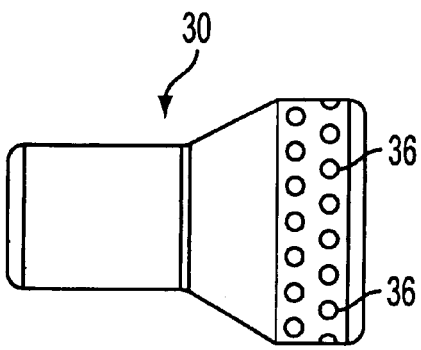
FIG. 1E is a side elevational view of a bell shaped diffuser.

FIGS. 1A through 1E illustrate various shapes in which a diffuser 30 may be formed. FIG. 1A illustrates a cylindrical shape, FIG. 1B illustrates an oval and/or round shape, FIGS. 1C-1 illustrates a semi-oval shape, FIGS. 1C-2 illustrates a semi-round shape, FIG. 1D illustrates a teardrop shape and FIG. 1E illustrates a bell shape. In addition, a diffuser 30 may be made of combinations of the shapes illustrated in FIGS. 1A–1E. The diffuser 30 configurations as shown in FIGS. 1A through 1E are intended to be exemplary only of the variety of configurations achievable with the present invention. It will be understood, based on this disclosure, that the present invention is not limited to the configurations shown in FIGS. 1A through 1E.

When used for continuous flow peritoneal dialysis, the diffuser 30 provides even disbursement of the dialysate 42. The plurality of openings 36 diffuse the delivery pressure of the dialysate 42, which can provide a gentle interaction on the peritoneal membrane 38.

It is to be understood that the dimensions of the invention may be varied for different size catheters, embodiments, and different characteristics unique to the user of the catheter. Examples of dimensions that may be used include the following: the proximal end of the diffuser 30 may be located less than 1 mm from the peritoneal membrane 38. Also, the distance between the distal end of the diffuser 30 and the beginning of the spiral at the distal end region 22 of the long lumen 14 may be approximately 15 cm in length. While the length of the spiral distal end region 22 of the long lumen 14 may vary, its length may be approximately 8.875 inches. Lumen resistance may yield in the range of 100 to 300 ml/min. When the diffuser 30 is cylindrical in shape, the width 28 of the cylinder 1A1 may be 0.5 cm long. While any number of openings 36 can be used, diffusers 30 may have openings in numbers ranging from six to twenty-four. It is to be understood that these dimensions are exemplary only, and are not to be taken as limitations on the invention.

As clearly illustrated in FIG. 4, the interior portion 32 of the diffuser 30 may have a proximal bonding region 82 and a distal bonding region 84, which are regions onto which the lumen wall 90 of the long lumen 14 may be bonded to the diffuser 30. The bonding may be accomplished by means of glue, adhesive, heat bonding, or other means currently known in the art or to be discovered.

Figure 5A:
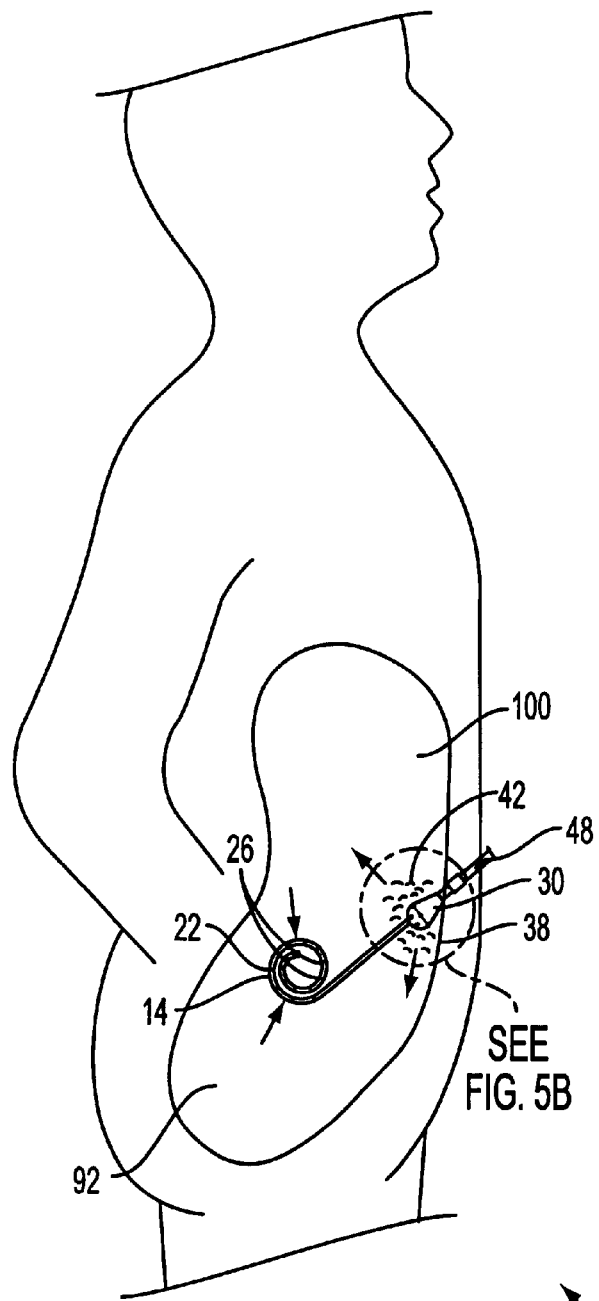
FIG. 5A shows the catheter in utility.
Figure 5B:
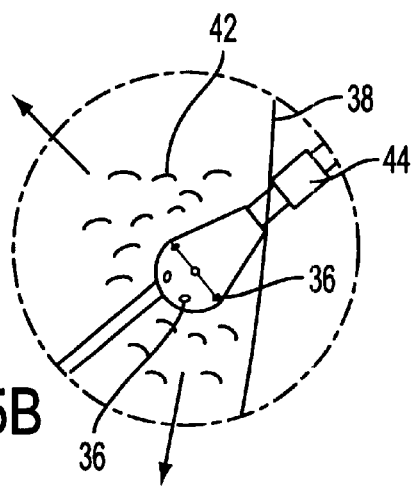
FIG. 5B is a view of the diffuser in utility.

Reference is now made to FIG. 5A, which shows the general location of the catheter 10 in the peritoneum 100, when the catheter 10 is used for continuous flow peritoneal dialysis. The diffuser 30 is located just distally to the peritoneal membrane 38. The coiled distal end region 22 of the long lumen 14 is located in the lower Douglas cavity 92 of the peritoneum 100. In use, the catheter 10 separates the delivery and return of the dialysate 42. As a result, there is minimal recirculation of the spent dialysate 42. In use, the fresh dialysate 42 enters the peritoneum 100 through the diffuser 30. The dialysate 42 passes through the peritoneum 100 where the necessary physiological and chemical processes occur, and which turn the fresh dialysate into spent dialysate. Constant intra-peritoneal volume can be maintained with high dialysate flow rates to maintain a high solute concentration gradient between plasma and continuously renewed dialysate solution 42. The spent dialysate 42 is aspirated back out of the peritoneum 100 through the at least one opening 26 of the long lumen 14.

The coiled design of the distal end region 22 of the long lumen 14 increases the bulk tubing which separates the parietal and visceral layers of the peritoneum 100 from obstructing the at least one distal opening 26 for outflow of the spent dialysate 42. The use of a plurality of openings 26 can increase the outflow rate. The use of a coiled long lumen 14 distal end region 22 is preferred for peritoneal dialysis because it is more gentle to the viscera than the tip of a straight lumen.

Preferably, the catheter 10, 10' is made of a low durometer silicone. However polyurethane or other biocompatible materials known in the art or to be developed may also be used. Low durometer silicone is preferable because of its biocompatibility and softness, which is beneficial for use in the peritoneum 100, which is a relatively soft body structure. In addition, low durometer silicone is flexible in a large range of temperatures and has no clinically harmful leachable plasticizers.

The first lumen 12, the second lumen 14, and additional lumens in catheters having more than two lumens, and the diffuser 30 may be made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, ployvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheter 10, 10' it is most preferred that the polymeric material includes a polyurethane or a polyolefin polymeric material having a preferably soft durometer, as specified below.

Suitable, preferred, biocompatible elastomers for use in forming the catheters 10, 10' include biocompatible elastomers such as medical grade silicone rubbers, polyvinyl chloride elastomers, polyolefin homopolymeric and copolymeric elastomers, urethane-based elastomers, and natural rubber or other synthetic rubbers. The catheter 10, 10' may be made of the elastomeric material such that they are flexible, durable, soft, and easily conformable to the shape of the area to be catheterized and/or the subcutaneous area and minimize risk of harm to vessel walls. If the catheter 10, 10' is used for hemodialysis applications, they may be formed of a soft silicone elastomer which has a hardness of at least about 80-A on a Shore durometer scale. Such an elastomer is available from Dow Corning, and can include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheter 10, 10' may also be radiopaque depending on its intended use.

Reference is now made to FIGS. 2B, 2C, 2D, 3, 5C, 5D and 6A through 6C, which show the invention with a hub 50, which is optional. When a hub 50 is provided, the proximal ends 16, 18 of the at least two lumens 12, 14 are located in the hub 50. The lumens 12, 14 may be attached to the hub 50 in a nonremovable manner, as seen in FIG. 2B. Alternatively, the lumens 12, 14 may be attached to a detachable hub 50¹, as seen in FIG. 2C. Detachable hubs are disclosed in a pending application, U.S. Provisional Application Serial No. 60/329,593, entitled "Detachable Hub," which is incorporated herein by reference. In addition, as illustrated in FIGS. 2D and 3, the use of all hubs 110 currently known in the art or to be discovered are within the scope of the invention. However, as illustrated in FIG. 2A, the hub is optional, and the hubs included for exemplary purposes should not be construed as limiting. One skilled in the art will appreciate that the catheter 10, 10' of the current invention may be used with a hub 50, a detachable hub 50¹, with no hub, or with hubs 110, or other attachments 110, currently known in the art or to be discovered.

In an embodiment of the invention, as seen in FIGS. 2B, 5C, 5D and 6A–6C, a non-removable hub 50 may be utilized. As seen in these figures, the proximal ends 16, 18 of the at least two lumens 12, 14 end in the hub 50. In addition, the distal ends of extenders 56, 58 also end in the hub 50. In this embodiment, when the lumens 12, 14 are "D" shaped, the proximal end openings 102, 104 of the lumens 12, 14 each are "D" shaped. Further, as seen in the embodiment illustrated in FIGS. 6A through 6C, the distal openings 106, 108 of the extenders 56, 58 each may have a round shape. The extension distal end openings 106, 108 and the proximal end openings, 102, 104 of the at least two lumens 12, 14 are brought into fluid communication with each other via hub channels 52, 54 molded in the hub 50. The hub 50 is molded around a removable interior pin (not shown) that is round at one end and "D" shaped at the other end. The shapes, sizes, and number of the lumens and extenders utilized with the hub 50 are exemplary, and not intended to be limiting. The extension proximal ends (not shown) are preferably connected to respective female luer locks (not shown) in a conventional manner. If decided, the female luer locks may be substituted with any suitable type of quick connect fittings, ferrule connectors, threadable connectors, or any connection means known in the art or to be discovered to achieve the flow of matter through the catheter 10, 10'. The extenders, as known in the art, may be connected in fluid communication to respective fluid inlets and outlets of the dialysis unit, other fluid transfer equipment, or other apparatus needed to carry out the purpose for the catheter 10, 10'.

As previously mentioned, the hub 50, 50' and extenders 56, 58 of the catheter 10, 10' are optional. The proximal end of the catheter 10, 10' of the present invention can be formed simply as at least two lumens 12, 14. The proximal ends 16, 18 of the lumens could be made connectable to dialysis equipment or other apparatus by providing luers or other connectors to the proximal ends 16, 18 of the lumens without a hub or additional extenders.

Figure 5C:
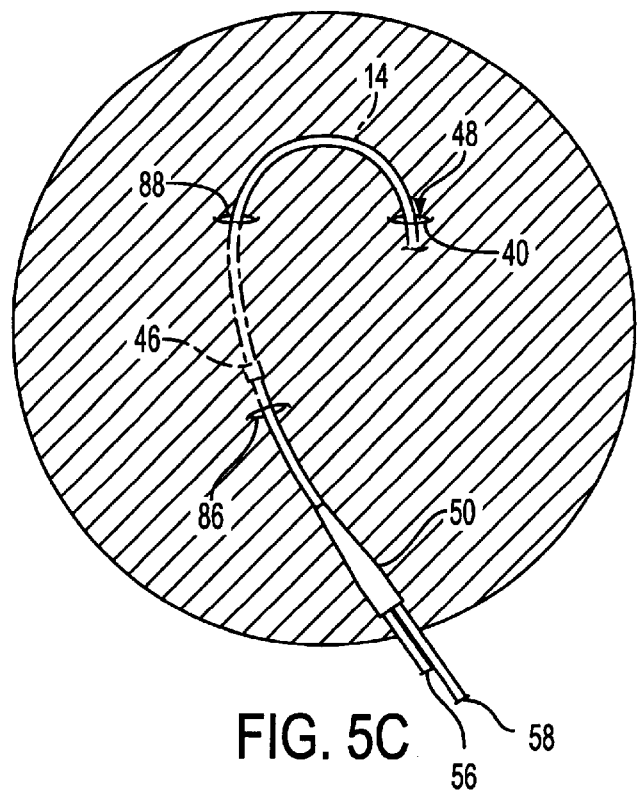
FIG. 5C is a view of a tunneled proximal end.
Figure 5D:
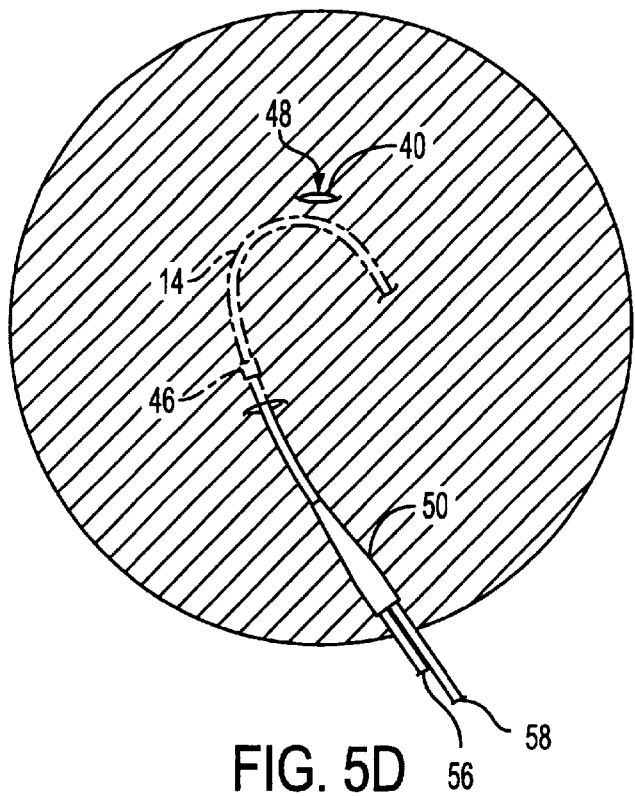
FIG. 5D is a view of a tunneled proximal end.

When the catheter 10, 10' has a hub 50 that is not detachable, generally, the hub 50 will be passable through the subcutaneous layer 48 of the body of the user of the catheter. As seen in FIGS. 5C and 5D, the lumen proximal ends 16, 18, the hub 50 and the extenders 56, 58 may be passed through a subcutaneous tunnel in the subcutaneous layer 48 of the body using various tunneling techniques. The lumen proximal ends 16, 18, the hub 50 and the extenders 56, 58 may be inserted in a tunnel entrance incision 86 and tunneled through the subcutaneous layer 48 to the tunnel exit incision 86. Alternatively, the lumen proximal ends 16, 18, the hub 50 and the extenders 56, 58 may be inserted in the catheter entrance incision 110 and tunneled through the subcutaneous layer 48 to a tunnel exit incision 86. In like manners, in catheters 10, 10' that do not have hubs or that have detachable hubs 50', the lumen proximal ends 16, 18 may be subcutaneously tunneled.

Reference is now made to FIGS. 2A through 2D, 3, 4, and 5A–5D, which illustrate the inclusion of at least one cuff 44, which is optional. In addition, a second cuff 46 may also be included, which is optional. The at least one cuff 44, as known in the art, is made of a material, generally polyester, onto which the tissue of the user of the catheter may grow in order to secure the catheter 10, 10' to the body of the user. A cuff 44 is located just proximally to the peritoneal membrane 38, when the catheter 10, 10' is used for continuous flow peritoneal dialysis. The cuff 44 may be located between 0 and 5 mm proximally from the peritoneal membrane 38. If the peritoneal membrane 38 is sutured at the incision site of the catheter 10, 10', added space may be needed because the suture, when pulled, may create folds in the membrane 38. Preferably, the space between the diffuser 30 and the cuff 44 will be in the range of between 0.5 and 10 mm. The range of distance between the first cuff 44 and the second cuff 46, preferably will be 10 cm. It is to be understood that the dimensions relating to the cuffs 44, 46 may be varied for different size catheters, embodiments, and different characteristics unique to the user of the catheter. The dimensions listed are not intended to be limiting, rather they are included for exemplary purposes.

As seen in FIGS. 5C and 5D, a second cuff 46 may located under the skin distally to the exit hole 86 for the catheter 10, 10'.

Figure 7:
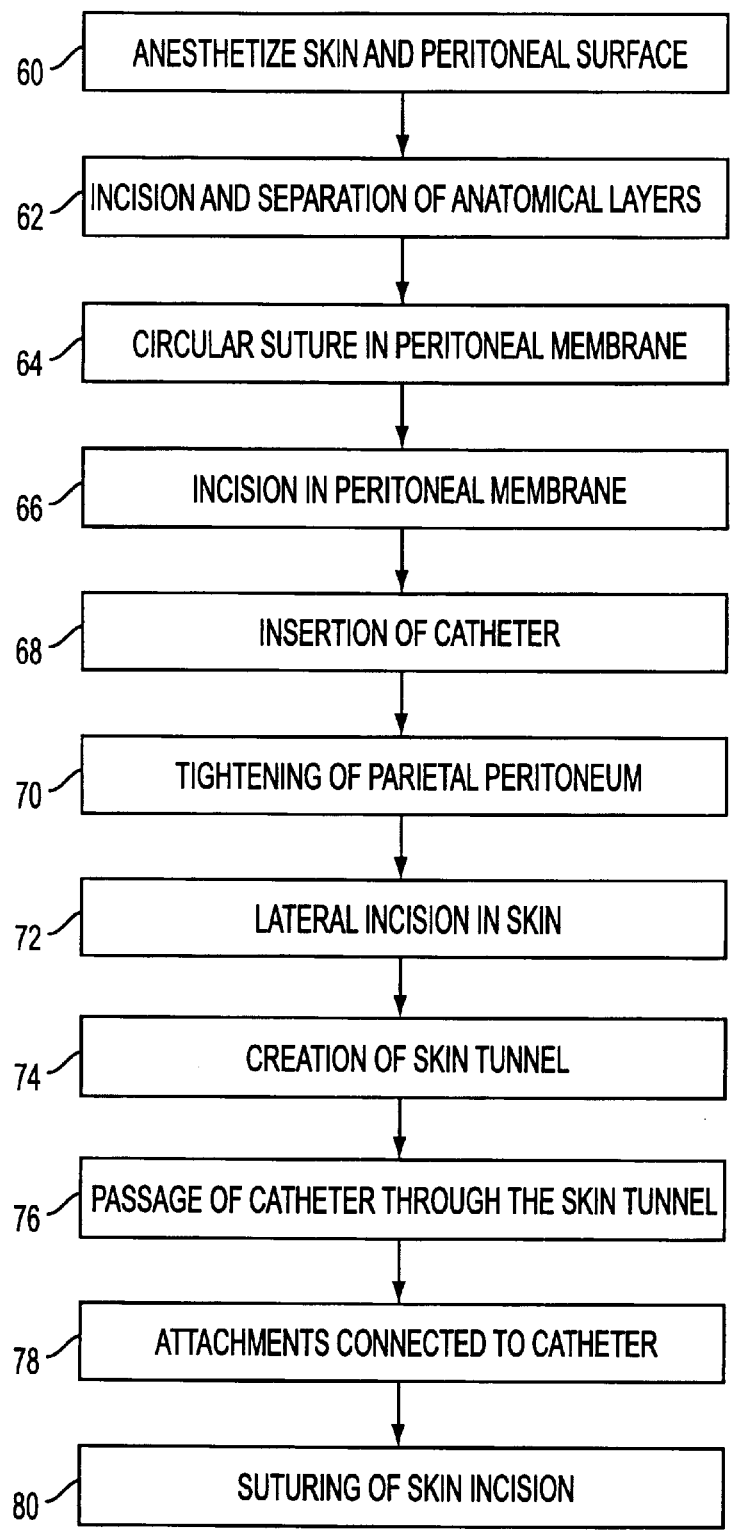
FIG. 7 is a flow chart of a method for continuous flow peritoneal dialysis.

Reference is now made to FIG. 7, which is a flowchart for the method for continuous flow peritoneal dialysis of the current invention. The method includes creating an incision in the body of the user and separating anatomical layers until the peritoneum is found 62; making a circular suture in the peritoneal membrane 64; inserting the distal end of the catheter into the Douglas cavity of the peritoneum, guided by a semi-rigid wire inside the outflow lumen, and tightening the parietal peritoneum between the diffuser and cuff by tightening the circular suture in the peritoneal membrane 68. In addition, the method may include, anesthetizing under the skin down to the peritoneal surface with a syringe 60. Also, the method may include making a lateral incision in the skin of the user 70; creating a subcutaneous tunnel, also known as a skin tunnel 72; passing the proximal end of the catheter subcutaneously through the skin tunnel 74, which may be accomplished by means of a tunneler; attaching connecting attachments to the lumens 76; and suturing the incision in the skin 78.

The method may also include providing a catheter 10 that has a diffuser 30.

The incision of step 62 may be about 3 cm long, and the incision of step 70 may be about 10 cm long. It is to be understood that the dimensions of the incisions may be varied for different size catheters, embodiments, and different characteristics unique to the user of the catheter. The dimensions listed are not intended to be limiting, rather they are included for exemplary purposes.

A sheath (not shown), as commonly known in the art, may be inserted over the diffuser before insertion of the catheter 10 into the body. Because the diffuser 30 preferably is made of a low durometer silicone, it may be easily compressed into the optional sheath. The sheath diminishes the volume of the diffuser 30, which may enable the insertion of the catheter 10, including the diffuser 30, utilizing a smaller incision than would be possible without use of a sheath. A Quill sheath is commonly known in the art, and may be used for a catheter 10 that does not have a hub. If the catheter 10 has a hub 50, which is not removable, a tear-away sheath, which is commonly known in the art, may be used.

When a catheter 10, 10' having a hub 50 which is not detachable is passed through the skin tunnel subcutaneously 76, the subcutaneous layer 48 will have to stretch to enable the hub 50 to pass. Normally, the elasticity of the subcutaneous layer 48 will enable the subcutaneous tissue to encapsulate the lumens 12, 14 after passage of the hub 50. When a detachable hub 501 is utilized on the catheter 10, 10', the hub 501 is among the attachments connected to the catheter during the step 76 of connecting attachments to the catheter.

As known in the art, the open ends of the luer locks may be connected in fluid communication to respective fluid inlets and outlets of the dialysis unit, or other fluid transfer equipment in order to begin dialysis.

Although the invention has been described and illustrated by various embodiments, it will be apparent to those of ordinary skill in the art that changes and modifications could be made which clearly fall within the scope of the invention. It is understood, therefore, that the invention is intended to be protected broadly within the spirit and scope as defined by the appended claims.

What is claimed is:

1. A continuous flow catheter, said catheter comprising at least two independent lumens, each of said at least two independent lumens having a proximal end and a distal end region, each of the distal end regions of each of said at least two independent lumens comprising at least one opening for the passage of matter into or out of the body of the user of the catheter, at least one of said at least two independent lumens being a first lumen and at least one of said at least two independent lumens being a second lumen, said second lumen being longer than said first lumen, wherein said distal end region of said second lumen is coiled.

2. The continuous flow catheter of claim 1, wherein matter passes into the body of the user of the catheter through said first lumen, and matter is removed from the body of the user of the catheter through said second lumen.

3. The continuous flow catheter of claim 2, said catheter further comprising a diffuser, said diffuser located over the at least one opening in said first lumen.

4. The continuous flow catheter of claim 3, said second lumen extending beyond said diffuser more distally into the body of the user of the catheter.

5. The continuous flow catheter of claim 4, said second lumen extending through said diffuser.

6. The continuous flow catheter of claim 1, wherein said catheter is used for peritoneal dialysis.

7. The continuous flow catheter of claim 6, said catheter further comprising at least one cuff.

8. The continuous flow catheter of claim 7, wherein one of said at least one cuff is located proximally to the peritoneal membrane.

9. The continuous flow catheter of claim 1, said catheter further comprising a hub, said proximal ends of said at least two lumens located in said hub.

10. The continuous flow catheter of claim 9, wherein said hub is passable subcutaneously through the body of the user of the catheter.

11. The continuous flow catheter of claim 9, wherein said hub is detachable.

12. The continuous flow catheter of claim 1, wherein each of said lumens is "D" shaped.

13. The continuous flow catheter of claim 1, wherein at least one of said at least two lumens contains a radiopague strip.

14. The continuous low catheter of claim 1, wherein said distal end region of said second lumen has at least one opening in the side of the lumen for the passage of matter.

15. The continuous flow catheter of claim 14, wherein said distal end region of said second lumen has a plurality of openings on the side of the lumen for the passage of matter.

16. The continuous flow catheter of claim 15, wherein said plurality of openings are located on the inside of said coil.

17. In a catheter for the passage of matter to the body of the user of the catheter, a compressible diffuser through which matter is dispensed into the body, wherein the diffuser is disposed about a separate lumen extending through the diffuser.

18. The diffuser of claim 17, wherein said diffuser has an interior portion and an exterior portion and at least one opening between said interior portion and said exterior portion, the matter to be dispensed by said catheter entering said diffuser and being dispensed in the body through said at least one opening.

19. The diffuser of claim 18, wherein said diffuser has a plurality of openings and the matter being dispensed in a diffused manner.

20. The diffuser of claim 19, wherein said plurality of openings are located radially around the sides of said diffuser.

21. The diffuser of claim 17, wherein said diffuser has a shape selected from the group consisting of cylindrical, teardrop, bell, round, oval, semi-round, semi-oval and a combination of shapes.

22. The diffuser of claim 17, wherein said diffuser is on a catheter used for peritoneal dialysis.

23. The diffuser of claim 22, wherein said dialysis is continuous flow peritoneal dialysis.

24. A catheter comprising at least two lumens, each of said at least two lumens having a proximal end and a distal end region, each of the distal end regions of each of said at least two lumens comprising at least one opening for the passage of matter into or out of the body of the user of the catheter, one of said at least two lumens being a first lumen and one of said at least two lumens being a second lumen, said second lumen being longer than said first lumen; said matter passing into the body of the user of the catheter through said first lumen, and said matter being removed from the body of the user of the catheter through said second lumen; said catheter further comprising a diffuser, said diffuser located over the at least one opening in said first lumen and said second lumen extending more distally in the body of the user through said diffuser; said diffuser having an interior portion and an exterior portion and more than one opening between said interior portion and said exterior portion; the matter to be dispensed by said catheter entering said diffuser and being dispensed in the body through said more than one opening in a diffused manner.

25. The catheter of claim 24, wherein said catheter is used for continuous flow peritoneal dialysis.

26. The catheter of claim 25, wherein said distal end region of said second lumen is coiled, said distal end region of said second lumen having a plurality of openings for the passage of matter.

27. The catheter of claim 26, wherein said openings are located on the inside of said coil.

28. The catheter of claim 25, said catheter further comprising at least one cuff.

29. The catheter of claim 28, wherein one of said at least one cuff is located proximally to the peritoneal membrane.

30. The catheter of claim 24, said catheter further comprising a hub, said proximal ends of said at least two lumens located in said hub.

31. The catheter of claim 30, wherein said hub is passable subcutaneously through the body of the user of the catheter.

32. The catheter of claim 30, wherein said hub is detachable.

33. The catheter of claim 24, wherein each said lumens is "D" shaped.

34. The catheter of claim 24, wherein at least one of said at least two lumens contains a radiopague strip.

35. A continuous flow peritoneal dialysis catheter comprising at least two lumens, each of said at least two lumens having a proximal end and a distal end region, each of the distal end regions of each of said at least two lumens comprising at least one opening for the passage of matter into or out of the body of the user of the catheter, one of said at least two lumens being a first lumen and one of said at least two lumens being a second lumen, said second lumen being longer than said first lumen; said matter passing into the body of the user of the catheter through said first lumen, and said matter being removed from the body of the user of the catheter through said second lumen; said catheter further comprising a diffuser, said diffuser located over the at least one opening in said first lumen and said second lumen extending more distally in the body of the user through said diffuser; said diffuser having an interior portion and an exterior portion and more than one opening between said interior portion and said exterior portion; the matter to be dispensed by said catheter entering said diffuser and being dispensed in the body through said more than one opening in a diffused manner; said distal end region of said second lumen being coiled and having a plurality of openings located on the inside of said coil for the passage of matter; said catheter further comprising at least one cuff, said at least one cuffs being located proximally to the peritoneal membrane.

36. The continuous flow peritoneal dialysis catheter of claim 35, said catheter further comprising a hub, said proximal ends of said at least two lumens located in said hub.

37. The continuous flow peritoneal dialysis catheter of claim 36, wherein said hub is passable subcutaneously through the body of the user of the catheter.

38. The continuous flow peritoneal dialysis catheter of claim 36, wherein said hub is detachable.

39. The continuous flow peritoneal dialysis catheter of claim 35, wherein each said lumens is "D" shaped.

40. The continuous flow peritoneal dialysis catheter of claim 35, wherein at least one of said at least two lumens contains a radiopaque strip.

41. A continuous flow catheter, said catheter comprising at least two lumens, each of said at least two lumens having a proximal end and a distal end region, each of the distal end regions of each of said at least two lumens comprising at least one opening for the passage of matter into or out of the body of the user of the catheter, at least one of said at least two lumens being a first lumen and at least one of said at least two lumens being a second lumen, said second lumen being longer than said first lumen, wherein said distal end region of said second lumen is coiled; said catheter further comprising a diffuser, said diffuser located over the at least one opening in said first lumen.

* * * * *

UNITED STATES PATENT AND TRADEMARK OFFICE
CERTIFICATE OF CORRECTION

PATENT NO. : 6,749,580 B2
DATED : June 15, 2004
INVENTOR(S) : Jack Work et al.

It is certified that error appears in the above-identified patent and that said Letters Patent is hereby corrected as shown below:

<u>Title page,</u>
Item [75], should read -- Angela Gloukhoff Wentling --

Signed and Sealed this

Thirty-first Day of August, 2004

JON W. DUDAS
*Director of the United States Patent and Trademark Office*